(12) United States Patent
Proksa et al.

(10) Patent No.: US 6,381,298 B2
(45) Date of Patent: Apr. 30, 2002

(54) METHOD OF COMBINING RECONSTRUCTION IMAGES

(75) Inventors: Roland Proksa; Michael Grass, both of Hamburg; Thomas Köhler, Norderstedt, all of (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/732,587

(22) Filed: Dec. 8, 2000

(30) Foreign Application Priority Data

Dec. 8, 1999 (DE) .......................... 199 59 092

(51) Int. Cl.[7] .............................. A61B 6/00
(52) U.S. Cl. ................. 378/15; 378/4; 378/19
(58) Field of Search ............... 378/4, 19, 15; 250/363.1; 600/425; 382/154

(56) References Cited

U.S. PATENT DOCUMENTS

| | | | | |
|---|---|---|---|---|
| 5,625,660 A | * | 4/1997 | Tuy ........................ | 378/15 |
| 5,930,384 A | * | 7/1999 | Guillemaud et al. ........ | 382/154 |
| 6,104,775 A | * | 8/2000 | Tuy .......................... | 378/4 |
| 6,108,575 A | * | 8/2000 | Besson ...................... | 600/425 |
| 6,177,675 B1 | * | 1/2001 | Gagnon et al. .......... | 250/363.1 |

FOREIGN PATENT DOCUMENTS

| | | | | |
|---|---|---|---|---|
| EP | 0860696 | | 8/1998 | .......... G01N/23/04 |

* cited by examiner

*Primary Examiner*—David P. Porta
*Assistant Examiner*—Pamela R. Hobden
(74) *Attorney, Agent, or Firm*—John Vodopia

(57) ABSTRACT

Method and device for forming a 3D image of an object to be examined by combining at least two reconstruction images, acquired by an X-ray device, by weighted addition. Specifically, each reconstruction image is weighted with a respective weighting function which describes at least approximately the distribution of noise and/or the distribution of artifacts in the reconstruction image. The image quality of the resultant three-dimensional image is thus significantly improved.

17 Claims, 2 Drawing Sheets

METHOD OF COMBINING RECONSTRUCTION IMAGES

BACKGROUND OF THE INVENTION

1. Field of the Invention

The invention relates to a method of forming a 3D image of an object to be examined by:combining at least two reconstruction images. The invention also relates to an X-ray device which is particularly suitable for carrying out such a method.

2. Description of the Related Art

It is known to utilize two-dimensional projections of an object to be examined for the formation of a reconstruction image of the object to be examined; such projections have been acquired by means of an imaging system, for example an X-ray device such as a C-arm X-ray device, a computed tomography apparatus, a magnetic resonance tomography apparatus or an ultrasound device. Various reconstruction methods that utilize different algorithms, for example, the Feldkamp algorithm, are known for the reconstruction. They enable the formation of a reconstruction image of an object to be examined from two-dimensional projections acquired along a circular trajectory of the measuring device, that is, for example the X-ray source and the X-ray detector, around the object to be examined. However, this type of data acquisition usually does not provide adequate data for the inverse problem, that is, the reconstruction of a complete three-dimensional reconstruction image; this becomes apparent in particular in the so-called Radon space. For example, a data acquisition along a circular trajectory provides data only within a torus in the Radon space; this does not suffice for the formation of an exact three-dimensional reconstruction image for which data would be required within a complete sphere in the Radon space. Therefore, the Feldkamp algorithm is merely an approximation and yields a reconstruction image which is exact in the central layer whereas induced artifacts increase continuously as the distance from the central layer increases.

Granted, it is possible to mitigate this problem by combining data acquired along two or more trajectories. For example, from EP 860 696 A2 it is known to acquire projections along two semi-circular trajectories that extend at an angle of 60° relative to one another, to form a respective reconstruction image from the projections acquired alone each time one trajectory, and to add the two reconstruction images subsequently so as to form a 3D image. The image quality can thus be improved, but artifacts still occur in the 3D image.

OBJECTS AND SUMMARY OF THE INVENTION

Therefore, it is an object of the invention to provide a method and an X-ray device for forming a 3D image of an object to be examined while improving the image quality.

This object is achieved. by means of a method in which at least two reconstruction images are combined by weighted addition, each reconstruction image being weighted with a weighting function which describes at least approximately the distribution of noise and/or artifacts in the reconstruction image, and by means of an X-ray device including an X-ray source and an X-ray detector that are rotatable about the object to be examined in order to acquire projections from different X-ray positions. The X-ray device also includes a reconstruction unit for forming reconstruction images from respective sets of projections acquired along different trajectories. In the X-ray device, a processor forms a 3D image of the object by combining at least two reconstruction images by weighted addition, each reconstruction image being weighted by a weighting function that describes at least approximately the distribution of noise and/or artifacts in the reconstruction image.

The invention is based on the recognition of the fact that noise and artifacts occurring in the reconstruction image are transferred to the resultant 3D image when two or more reconstruction images are simply added. The noise is due essentially to the hardware used, in particular the detector elements used, for example the X-ray detector, whereas the cause of the artifacts lies mainly in the fact that not all data necessary for an exact reconstruction can be acquired from projections acquired alone, a trajectory. Depending on the reconstruction algorithm used, a different type of noise and different artifacts are thus induced in a reconstruction image. In order to reduce the transfer of such noise or such artifacts from a reconstruction image to a resultant 3D image, the invention proposes to determine a weighting function for each reconstruction image, which weighting function at least approximately describes the distribution of noise and/or artifacts in the reconstruction image, to multiply the reconstruction image by the weighting function, and to add all reconstruction images thus weighted so as to form a resultant 3D image only after that.

In preferred further versions of the method in accordance with the invention the weighting functions are determined by simulations or measurements performed on a phantom object, or use is made of mathematical functions, for example functions which descend linearly or as a square root (or vary otherwise), for example, from the center to the edge of the reconstruction image to be weighted by the respective weighting function. The image quality of the resultant 3D image can be significantly improved in comparison with the known method even while using such simple mathematical functions as weighting functions.

Further improvements still can be achieved when the weighting function is adapted as accurately as possible to the distribution of the noise or the distribution of artifacts occurring in a reconstruction image. It may be arranged such that for each pixel or group of pixels of a reconstruction image there is assigned a value of the associated weighting function, so that each pixel or each croup of pixels can be individually weighted in dependence on the magnitude of the noise component or artifact component of this pixel or this group of pixels.

In a particularly attractive version of the methods the weighting functions are chosen in such a manner that artifacts and noise are separately weighted for each pixel or each group of pixels of a reconstruction image. This enables advantageous selection of the preferred type of disturbance and the location in the 3D image in which such disturbances are to be suppressed.

The invention is used particularly advantageously in an X-ray device that is provided with an X-ray source that generates a conical X-ray beam and with a two-dimensional X-ray detector, the X-ray source and the X-ray detector rotating about the object to be examined in order to acquire the projections. The X-ray device may be, for example, a C-arm X-ray unit. In principle, however, the invention can also be used in a computed tomography apparatus.

BRIEF DESCRIPTION OF THE DRAWINGS

The invention will be described in detail hereinafter with reference to the drawings. Therein.

DETAILED DESCRIPTION OF THE PREFERRED EMBODIMENT.

Figure 1:
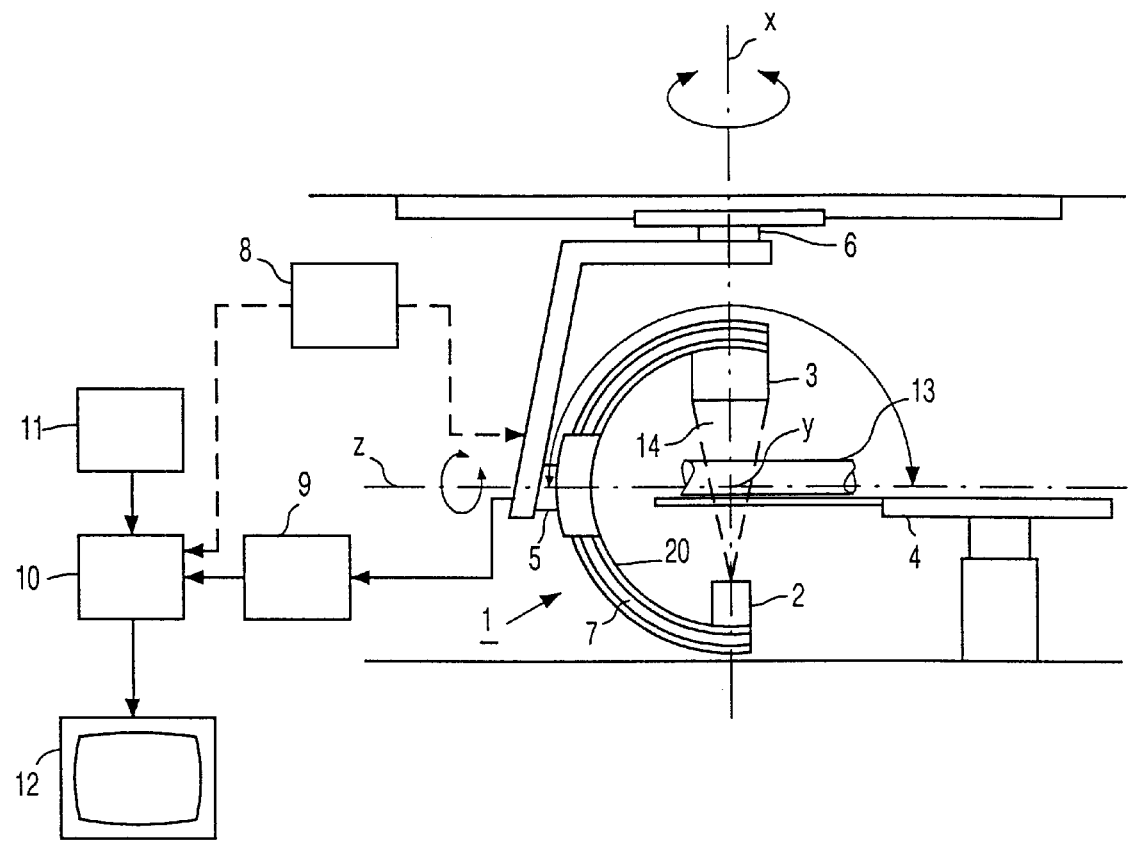
FIG. 1 shows a C-arm X-ray unit in accordance with the invention.

The C-arm X-ray unit 1 shown in FIG. 1 includes an X-ray source 2 which is arranged at one end of the C-arm and an X-ray detector 3 which is arranged at the other end of the C-arm 20. The X-ray tube generates a conical X-ray beam 14 which traverses an object 13 to be examined, for example a patient, arranged on a patient table 4 in the examination zone, after which it is incident on the two-dimensional X-ray detector 3. In the position shown the X-ray tube 2 and the X-ray detector 3 are rotatable about the y axis via rails 7 provided on the C-arm 20. As a result of the suspension by way of several arms and hinges 5, 6, the position of the C-arm 20 can be changed in various directions; for example, the C-arm 20 is capable of rotation about the x axis and the z axis. The control of these motions for the acquisition of projections from different X-ray positions and of the data acquisition is performed by means of a control unit 8. The projections acquired are applied to a reconstruction unit 9 which forms a respective reconstruction image from the projections. acquired along a trajectory. These reconstruction images, formed each time from a respective set of projections acquired along different trajectories, are subsequently applied to an arithmetic unit 10 which, in conformity with the method in accordance with the invention, divides each reconstruction image by a weighting function stored in a storage unit 11, the result subsequently being added and normalized. The arithmetic unit 10 is also controlled by the control unit 8. The resultant 3D image can be displayed on a monitor 12.

Figure 2:
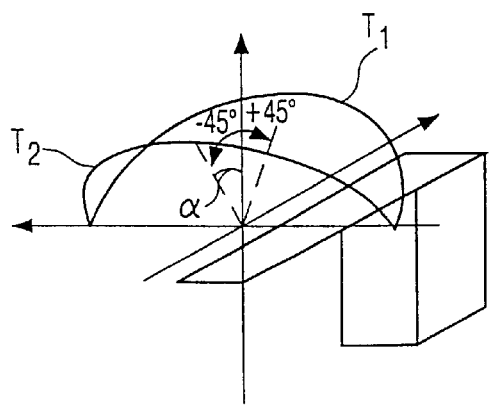
FIG. 2 shows diagrammatically two trajectories followed during the acquisition of projections.

FIG. 2 shows diagrammatically two trajectories $T_1$ and $T_2$. Each trajectory describes the path traveled by the center of the detector surface of the X-ray detector 3 during the acquisition of projections. Therefore, the trajectory is the curve through all X-ray positions in which a respective projection has been acquired. In the case shown the trajectories $T_1$ and $T_2$ describe a respective semi-circle and are tilted through an angle of $2\alpha=90°$ relative to one another. A first reconstruction image is formed from the projections acquired along the trajectory $T_1$ whereas a second reconstruction image is formed from the projections acquired along the trajectory $T_2$. Subsequently, the two reconstruction images are combined so as to form a resultant 3D image in accordance with the invention; this will be described in detail hereinafter with reference to FIG. 3.

Figure 3:
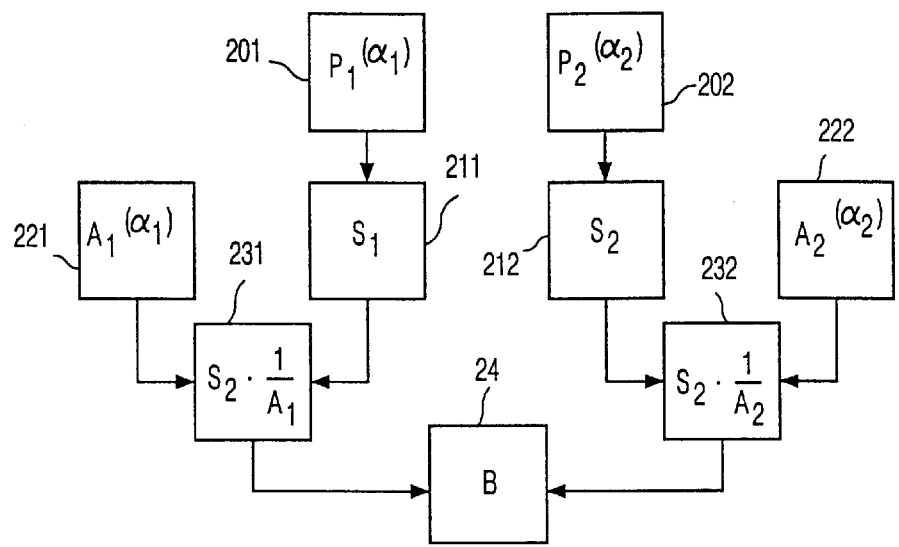
FIG. 3 shows a flow chart illustrating the method in accordance with the invention.

The blocks 201 and 202 of the flow chart shown in FIG. 3 symbolically contain two sets of projections $P_1(\alpha_1)$ and $P_2((\alpha_2)$ as starting points determined along two trajectories $T_1$ and $T_2$, respectively, that extend at the angles $\alpha_1$ and $\alpha_2$, respectively, relative to a reference plane. From each of these sets of projections $P_1$, $P_2$ a reconstruction image $S_1$, $S_2$ is determined in the blocks 211 and 212. In the blocks 231 and 232 the reconstruction images $S_1$ and $S_2$ are divided by the weighting, functions $A_1(\alpha_1)$ and $A_2(\alpha_2)$, adapted to the relevant reconstruction image, or multiplied by the inverse weighting functions $1/A_1(\alpha_1)$ and $1/A_2(\alpha_2)$. The weighting functions $A_1$, $A_2$ are stored in the blocks 221 and 222 and are determined in advance, for example, by means of a simulation calculation performed on a phantom object. Finally, in the block 24 the reconstruction images thus weighted are combined by addition and normalization so as to form one 3D image B which, depending on the quality of the weighting functions, exhibits significantly less noise and artefacts than a 3D image formed by simple addition of two non-weighted reconstruction images.

The formation of the 3D image B can also be described in general in the form of a formula for the case involving, combination of n reconstruction images $S_n$:

$$B = \frac{\sum_n S_n A_n^{-1}}{\sum_n A_n^{-1}}$$

It may also be arranged that a distinction is made between noise and artifacts during the weighting by means of the weighting functions; the sum of these two sub-weighting operations then has to be 1 for each pixel. This can also be expressed in the form of a formula for a general case:

$$B = \frac{\sum_n S_n(w_n R_n^{-1} + (1 - w_n)K_n^{-1})}{\sum_n w_n R_n^{-1} + (1 - w_n)K_n^{-1}}$$

$K_n$ is the artifact distribution function for the reconstruction image n, $R_n$ is the noise distribution function for the reconstruction image n, and $W_n$ is the weight distribution that weights the suppression of noise and artifacts in a reconstruction image, that is, enables a decision to be taken as regards the ratio of suppression of artifacts to suppression of noise in a reconstruction image.

The method in accordance with the invention enables a significant improvement in respect of the suppression of noise and artifacts in a 3D image. Generally speaking, the improvement of the signal-to-noise ratio that can be theoretically achieved by addition of n reconstruction images amounts to √n in comparison with the signal-to-noise ratio of a single reconstruction image, provided that the noise component in all n reconstruction images is approximately the same; however, this is only rarely the case in practice. In practice, therefore, this improvement by the known addition of reconstruction images is generally significantly less. Assuming that artifacts in different reconstruction images are not correlated, the method in accordance with the invention, however, enables an improved signal-to-noise ratio to be obtained which may amount to as much as √n, depending on the quality of the weighting functions.

Figure 4:
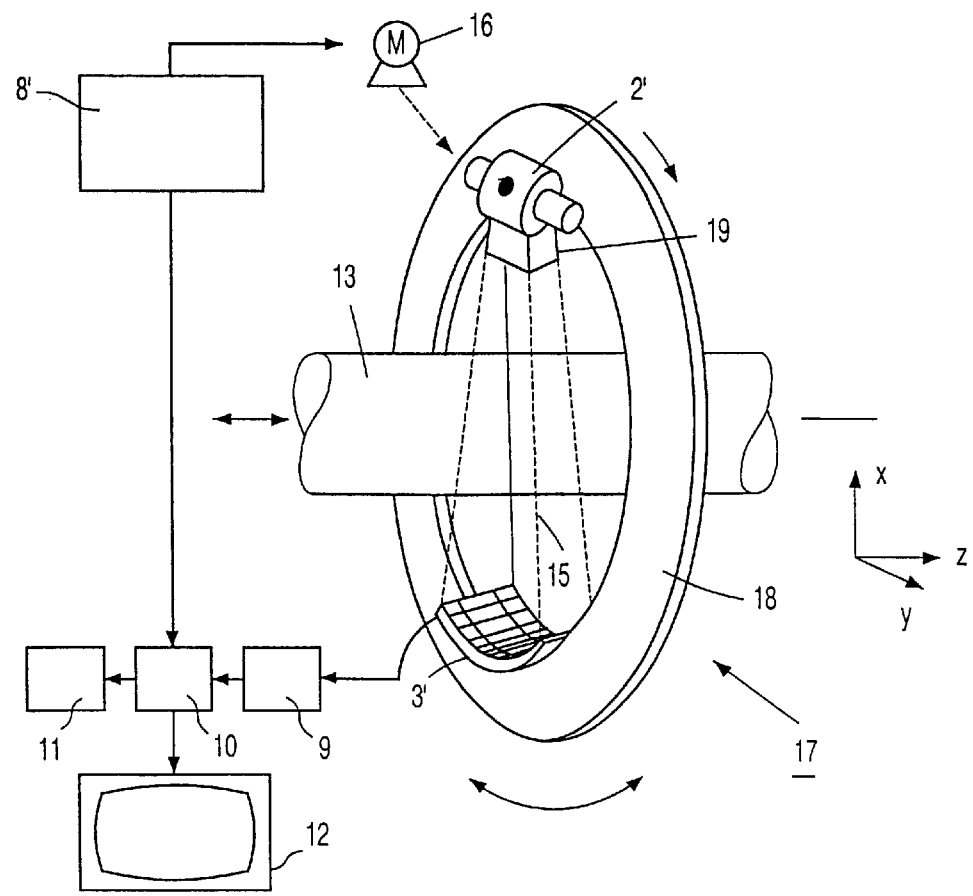
FIG. 4 shows a computed tomography unit in accordance with the invention.

FIG. 4 shows a computed tomography unit 17 in accordance with the invention. The X-ray device 2' includes a collimator 19 for forming a conical X-ray beam 15 that is mounted, together with the X-ray detector 3', on a ring-shaped gantry 18; they rotate about the object 13 to be examined, arranged along the z axis, in order to acquire projections; to this end, the gantry is controlled by a motor drive 16 which itself is controlled by the control unit 8'. The projections acquired are applied again to a reconstruction unit 19 in order to form reconstruction images which are applied again to the arithmetic unit 10. The 3D image is formed from said reconstruction images in the same way as described above for the C-arm X-ray unit.

The X-ray devices shown constitute merely exemplary embodiments of the invention. The invention, however, can also be used in other X-ray devices in which a 3D image that has been enhanced in respect of suppression of noise and artifacts is to be formed from a plurality of reconstruction images. The trajectories shown in FIG. 2 and the number of such trajectories are also given merely by way of example. The projections can also be acquired along other trajectories and also along more than two trajectories, for example two or more parallel full circles or two full circles extending perpendicularly to one another.

What is claimed is:

1. A method of forming a 3D image of an object to be examined, comprising the step of combining at least two reconstruction images by weighted addition, each reconstruction image being weighted with a weighting function which describes at least approximately at least one of the distribution of noise and the distribution of artifacts in said reconstruction image.

2. A method as claimed in claim 1, wherein each weighting function describes at least approximately the distribution of noise and the distribution of artifacts in the reconstruction image to be weighted thereby.

3. A method as claimed in claim 1, further comprising the step of determining the weighting functions by simulation.

4. A method as claimed in claim 1, wherein the weighting functions are in the form of mathematical functions.

5. A method as claimed in claim 1, further comprising the step of selecting the weighting functions such that artifacts and noise are separately weighted for each pixel of a reconstruction image.

6. A method as claimed in claim 1, further comprising the step of acquiring the reconstruction images by means of an imaging medical system.

7. A method as claimed in claim 1, further comprising the step of deriving the reconstruction images from a plurality of projections acquired by means of an X-ray device which includes a radiation source that generates an X-ray beam and rotates about the object, and an X-ray detector that rotates about the object.

8. An X-ray device for examining an object, comprising:
   an X-ray source and an X-ray detector adapted to be rotatable about the object for acquiring projections from different X-ray positions,
   a reconstruction unit for forming reconstruction images from each respective set of projections acquired by said X-ray detector, the individual sets of projections being acquired along different trajectories of said X-ray detector, and
   a processor for forming a 3D image of the object by combining at least two of said reconstruction images by weighted addition, each reconstruction image being weighted by a weighting function that describes at least approximately at least one of the distribution of noise artifacts in said reconstruction image.

9. An X-ray device as claimed in claim 8, wherein said X-ray source and said X-ray detector are arranged to provide and detect, respectively, a conical X-ray beam.

10. An X-ray device as claimed in claim 8, wherein said X-ray device is a C-arm X-ray unit or a computed tomography unit.

11. A method as claimed in claim 1, further comprising the step of determining the weighting functions by measurement performed on a phantom object.

12. A method as claimed in claim 1, wherein each of the weighting function is a mathematical function that descends linearly from a center to an edge of the reconstruction image to be weighted.

13. A method as claimed in claim 1, wherein each of the weighting function is a mathematical function that descends as a square root from a center to an edge of the reconstruction image to be weighted.

14. A method as claimed in claim 1, further comprising the step of acquiring the reconstruction images by means of an imaging medical system selected from a group consisting of an X-ray device, an ultrasound device, a magnetic resonance tomography apparatus or a computed tomography apparatus.

15. A method as claimed in claim 1, further comprising the step of deriving each of the reconstruction images from a respective set of projections acquired by an X-ray detector, the respective sets of projections being acquired along different trajectories of the X-ray detector.

16. A method as claimed in claim 1, further comprising the step of forming the reconstruction images by acquiring a first set of projections from an X-ray detector upon receipt of X-rays passing through the object while the X-ray detector is in a first trajectory of motion, combining the first set of projections without weighting into a first reconstruction image, changing the trajectory of motion of the X-ray detector, acquiring a second set of projections from the X-ray detector upon receipt of X-rays passing through the object while the X-ray detector is in the changed trajectory of motion, and combining the second set of projections without weighting into a second reconstruction image.

17. A method of forming a 3D image of an object to be examined by combining at least two reconstruction images by weighted addition, each reconstruction image being weighted with a weighting function which describes at least approximately at least one of the distribution of noise and artifacts in said reconstruction image, the weighting functions being selected such that artifacts and noise are separately weighted for each pixel of a reconstruction image.

* * * * *